United States Patent [19]

Racchini et al.

[11] Patent Number: 5,458,568
[45] Date of Patent: Oct. 17, 1995

[54] POROUS BALLOON FOR SELECTIVE DILATATION AND DRUG DELIVERY

[75] Inventors: Joel R. Racchini, Edina; James E. Shapland; Mark B. Knudson, both of Shoreview; Jin Shimada, Falcon Heights, all of Minn.; Keith R. Hildebrand, Houlton, Wis.

[73] Assignee: CorTrak Medical, Inc., Minneapolis, Minn.

[21] Appl. No.: 123,374

[22] Filed: Sep. 17, 1993

Related U.S. Application Data

[63] Continuation-in-part of Ser. No. 937,464, Aug. 28, 1992, Pat. No. 5,286,254, which is a continuation-in-part of Ser. No. 705,731, May 24, 1991, abandoned.

[51] Int. Cl.$^6$ ............................................. A61N 1/30
[52] U.S. Cl. .............................................. 604/19; 604/96
[58] Field of Search ................... 604/19–22, 95–103; 601/2

[56] References Cited

U.S. PATENT DOCUMENTS

| | | |
|---|---|---|
| 578,611 | 3/1897 | Rively . |
| 725,731 | 4/1903 | Linn . |
| 873,021 | 12/1907 | Cool . |
| 2,123,980 | 7/1938 | Warwick . |
| 2,499,045 | 8/1948 | Walker et al. . |
| 3,542,014 | 11/1970 | Peronneau . |
| 3,865,108 | 2/1975 | Hartop . |
| 4,126,134 | 11/1978 | Bolduc et al. . |
| 4,137,906 | 2/1979 | Akiyama et al. . |
| 4,202,346 | 5/1980 | Granier . |
| 4,323,071 | 4/1982 | Simpson et al. . |
| 4,338,942 | 7/1982 | Fogarty . |
| 4,364,392 | 12/1982 | Strother et al. . |

(List continued on next page.)

FOREIGN PATENT DOCUMENTS

| | | |
|---|---|---|
| 299698 | 1/1989 | European Pat. Off. . |
| 372088 | 6/1990 | European Pat. Off. . |
| 2582946 | 12/1986 | France . |
| 147314 | 4/1981 | German Dem. Rep. . |
| 3915636 | 4/1990 | Germany . |
| 49-132888 | 12/1974 | Japan . |
| 588870 | 6/1977 | Switzerland . |
| 645273 | 9/1984 | Switzerland . |
| 1003853 | 3/1983 | U.S.S.R. . |

(List continued on next page.)

OTHER PUBLICATIONS

Antich, *Journal of Orthopaedic and Sports Physical Therapy*, 4(2), 99–102 (1982).
Brand, *Cardio*, Nov., 48–56 (1989).
Ellman et al., *Investigative Radiology*, 19(5), 416–423 (1984).
Goldman et al., *Artherosclerosis*, 65, 215–225 (1987).
Jorgensen et al., *The Lancet*, May 20, 1106–1108 (1989).
Klimberg et al., *Urology*, 33(2), 153–158 (1989).
Layer et al., *Br. J. Surg.*, 71, 709–710 (1984).
Okada et al., *Stroke*, 19(12), 1470–1476 (1988).
Okada et al., *Neurosurgery*, 25(6), 892–898 (1989).
Sheehan and Hrapchak, *Theory and Practice of Histotechnology*, Ch. 2, 40–50 (1984).
Skauen et al., *International Journal of Pharmaceutics*, 20, 235–245 (1984).
Wolinsky et al., *JACC*, 15(2), 475–481 (1990).
*BBI Newsletter*, 13(5), 85–91 (1990).

*Primary Examiner*—C. Fred Rosenbaum
*Assistant Examiner*—N. Kent Gring
*Attorney, Agent, or Firm*—Merchant, Gould, Smith, Edell, Welter & Schmidt

[57] ABSTRACT

A drug delivery apparatus and method for delivering a drug locally to internal body tissue. The invention contemplates positioning a drug delivery device in a body passageway or within body tissue and then selectively wetting a membrane within the device, making the membrane permeable and allowing transport of a drug across the membrane and into the passageway wall or body tissue.

9 Claims, 4 Drawing Sheets

U.S. PATENT DOCUMENTS

| | | |
|---|---|---|
| 4,383,529 | 5/1983 | Webster . |
| 4,403,612 | 9/1983 | Fogarty . |
| 4,551,132 | 11/1985 | Pasztor et al. . |
| 4,573,966 | 3/1986 | Weikl et al. . |
| 4,582,181 | 4/1986 | Samson . |
| 4,606,337 | 8/1986 | Zimmermann et al. . |
| 4,608,984 | 9/1986 | Fogarty . |
| 4,610,662 | 9/1986 | Weikl et al. . |
| 4,636,195 | 1/1987 | Wolinsky . |
| 4,663,358 | 5/1987 | Hyon et al. . |
| 4,689,041 | 8/1987 | Corday et al. . |
| 4,693,704 | 9/1987 | Ogita . |
| 4,698,058 | 10/1987 | Greenfeld et al. . |
| 4,705,507 | 11/1987 | Boyles . |
| 4,714,460 | 12/1987 | Calderon . |
| 4,733,665 | 3/1988 | Palmaz . |
| 4,744,366 | 5/1988 | Jang . |
| 4,767,402 | 8/1988 | Kost et al. . |
| 4,776,337 | 10/1988 | Palmaz . |
| 4,787,888 | 11/1988 | Fox . |
| 4,800,882 | 1/1989 | Gianturco . |
| 4,819,637 | 4/1989 | Dormandy, Jr. et al. . |
| 4,819,751 | 4/1989 | Shimada et al. . |
| 4,824,436 | 4/1989 | Wolinsky . |
| 4,832,688 | 5/1989 | Sagae et al. . |
| 4,866,050 | 9/1989 | Ben-Amoz . |
| 4,917,666 | 4/1990 | Solar et al. ............................... 604/96 |
| 4,948,587 | 8/1990 | Kost et al. . |
| 4,994,033 | 2/1991 | Shockey et al. . |
| 5,000,734 | 3/1991 | Boussignac et al. . |
| 5,007,897 | 4/1991 | Kalb et al. . |
| 5,041,107 | 8/1991 | Heil, Jr. . |
| 5,047,028 | 9/1991 | Qian . |
| 5,087,243 | 2/1992 | Avital . |
| 5,087,244 | 2/1992 | Wolinsky et al. . |
| 5,102,402 | 4/1992 | Dror et al. . |
| 5,232,444 | 8/1993 | Just et al. ................................. 604/96 |
| 5,236,413 | 8/1993 | Feiring . |
| 5,240,913 | 8/1993 | Maraganore et al. ..................... 623/11 |

FOREIGN PATENT DOCUMENTS

| | | |
|---|---|---|
| 4,411,648 | 10/1983 | Davis et al. . |
| 4,416,274 | 11/1983 | Jacobsen et al. . |
| 4,417,576 | 11/1983 | Baran . |
| 4,456,012 | 6/1984 | Lattin . |
| 4,509,523 | 4/1985 | Pevsner . |
| 1069827 | 1/1984 | U.S.S.R. . |
| 1069826 | 1/1984 | U.S.S.R. . |
| 1146057 | 3/1985 | U.S.S.R. . |
| 1410973 | 7/1988 | U.S.S.R. . |
| WO8901794 | 3/1989 | WIPO . |
| WO91/16945 | 11/1991 | WIPO . |
| WO91/19529 | 12/1991 | WIPO . |

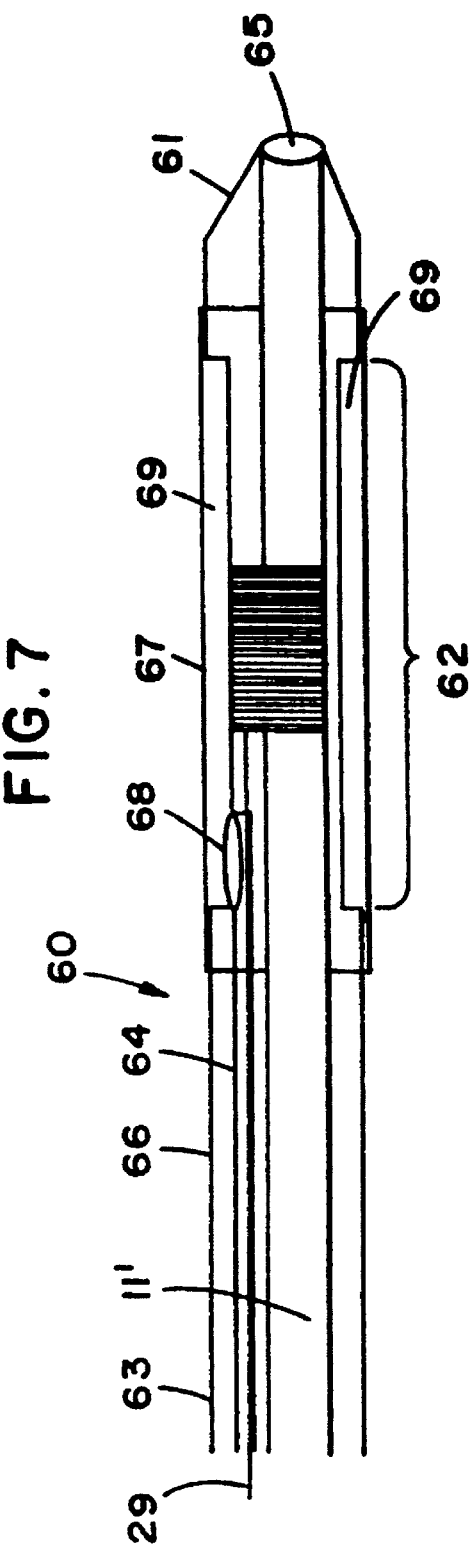
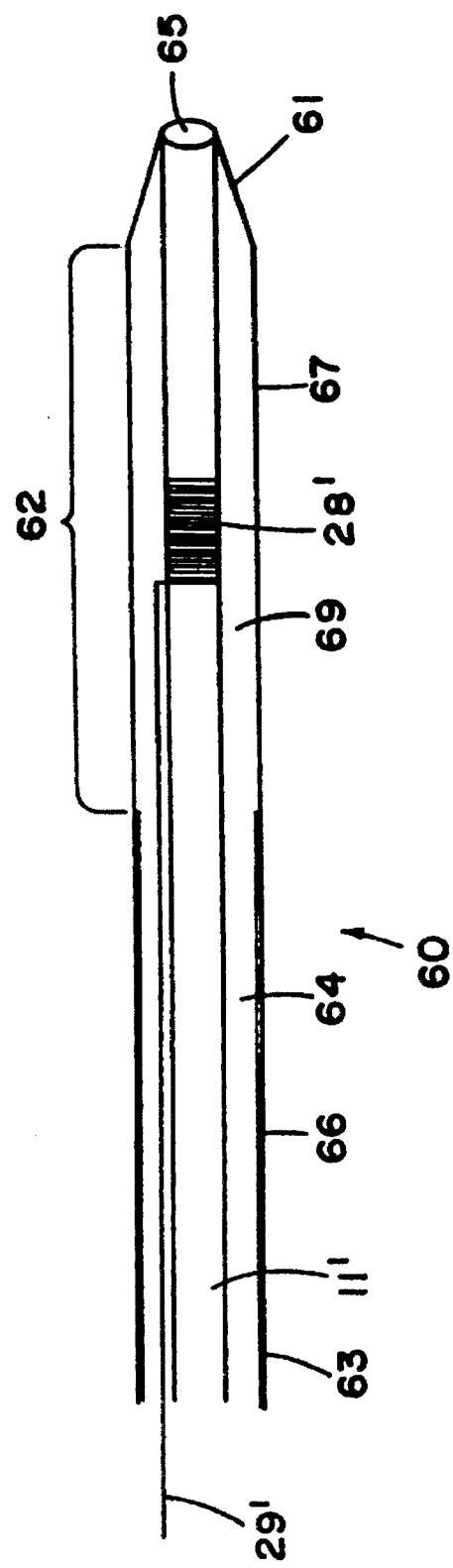

5,458,568

POROUS BALLOON FOR SELECTIVE DILATATION AND DRUG DELIVERY

REFERENCE TO APPLICATIONS

This application is a continuation-in-part of application Ser. No. 07/937,464, filed Aug. 28, 1992, now U.S. Pat. No. 5,286,254 which is a continuation-in-part of application Ser. No. 07/705,731, filed May 24, 1991 now abandoned, both of which are hereby incorporated by reference.

BACKGROUND OF THE INVENTION

1. Field of the Invention

The present invention relates generally to a drug delivery apparatus and method for selectively and locally delivering a drug to internal body tissue. More particularly, the present invention relates to an apparatus and method which can both dilate a passageway and deliver a drug selectively and locally to internal body tissue after or during dilatation using a single catheter.

2. Description of the Prior Art

Many techniques currently exist for delivering drugs or other medicaments to body tissue. These include, among possible others, oral administration, injection directly into body tissue such as through an intramuscular injection or the like, topical or transcutaneous administration where the drug is passively absorbed, or caused to pass, into or across the skin or other surface tissue and intravenous administration which involves introducing a selected drug directly into the blood stream.

Except for topical or transcutaneous administration, the above drug delivery systems tend to be systemic. In other words, administration of the drug is delivered throughout the body by the blood stream. Although transcutaneous drug delivery systems tend to be localized delivery systems in that the drug is delivered locally to a selected area, such drug delivery systems are also, by definition, limited to application of a drug externally through the patient's skin or other surface tissue. Thus, the above described drug delivery systems are generally not appropriate for the localized treatment of internal body tissue.

Although many medical situations are satisfactorily treated by the general systemic administration of a drug, there are a great many treatments which could be facilitated and/or improved by the ability to deliver or administer a drug locally to a selected portion of internal body tissue, without appreciably affecting the surrounding tissue.

One example is the ability to treat the dilated vessel in percutaneous transluminal coronary angioplasty (PTCA), and thus limit or prevent restenosis. In PTCA, catheters are inserted into the cardiovascular system under local anesthesia and an expandable balloon portion is then inflated to compress the atherosclerosis and dilate the lumen of the artery. Despite the general success of such PTCA procedures, high restenosis rates (reported to be as high as 47%) continue to be a major problem. Various techniques have been tried to treat stenosed vessels including the use of lasers, application of heat and the use of intravascular stents. However, many of these are still under investigation with mixed results, while others have generally not been successful. The ability to administer a drug locally to the dilated portion of the artery in PTCA procedures, without significantly affecting other tissues, would greatly enhance the ability to address the restenosis problem.

A second example of specific application for a local drug delivery system for delivering a drug to an internal body tissue is in the treatment of cancerous tumors or the like. In the treatment of such tumors, an objective is to administer the cancer drug so that it localizes, as much as possible, in the tumor itself. Such drugs are commonly administered systemically through the blood stream. Various means are then utilized for causing the drug to localize in the cancer tumor. Nevertheless, significant portions of the drug still circulate through the blood stream, thereby affecting non-cancerous tissue, producing undesirable side effects, and limiting the dosages of the drug which can be safely administered.

Furthermore, although devices are known which can provide for localized internal delivery of drugs or other substances and other devices are known which can perform dilatation of passageways, neither devices can typically be used to perform both dilatation and drug delivery.

Dilatation catheters cannot typically be used to deliver drugs because catheters which can be dilated typically consist of nonporous thermoplastic tubes molded into balloon geometries. The balloons are typically non-porous to allow for inflation with a fluid at pressures of up to 20 atmospheres without leakage of the fluid into the dilated vessel. Once the vessel is dilated, the non-porous balloon is removed and replaced with a device which is capable of delivering drug to the localized area. Such an exchange of the dilatation catheter with the appropriate drug delivery catheter results in additional time and expense, as well as overcoming the difficulties associated with returning the drug delivery catheter to the exact position of the balloon catheter when the original dilation was performed. Additionally, the time lapse between dilation and drug delivery can be significant if it affects the efficacy of the drug treatment.

Devices which can provide localized internal drug delivery have included a number of designs. Initial versions were simply dilatation catheters with a limited number of relatively large holes punched in the non-porous dilatation balloon material to render it porous. Although these balloons were capable of transferring drugs to a local internal area, they are ineffective at dilatation because of the large leakage through the pores punched through the balloons.

One attempt at providing a catheter for both dilatation and drug delivery has included coating a dilatation balloon with a drug containing matrix or microparticles which burst upon pressure to release a drug locally within a patient. In this design, the drug is exposed to the body throughout the procedure, including advancement of the catheter through the patient's body, thus offering the possibility of inadvertent and unwanted drug delivery during advancement of the catheter.

Yet another attempt includes the use of concentric porous and non-porous balloons in which the inner non-porous balloon is inflated to provide the dilatation and a drug is then provided to the space between the inner non-porous balloon and the outer porous balloon to provide local internal drug delivery. Such devices suffer from the complexity of manufacturing such a dual concentric balloon structure as well as the relatively large deflated profile of the balloon which can add to difficulties in placing the device within smaller vessels in patients.

Accordingly, there is a need in the art for a method and single apparatus which can both dilate a passageway and deliver a drug or other substance selectively and locally to internal body tissue after or during dilatation using a single catheter balloon which can be selectively made permeable.

SUMMARY OF THE INVENTION

In accordance with the present invention, an apparatus and method are provided for dilating a vessel and delivering drugs or other substances selectively and locally to the dilated vessel using a single device. The delivery can be performed either simultaneously during the dilatation or sequentially after dilatation. More specifically, the invention involves an apparatus and method for delivering a drug or other substance substantially transversely to the longitudinal axis of a body passageway such as blood vessel, urinary tract, intestinal tract, kidney ducts, etc., in order to treat a localized region of the passageway itself or to treat a localized region or tissue located adjacent to the passageway.

The invention also involves an apparatus and method for delivering a drug or combination of drugs directly to internal body tissue which may or may not be dilated. In that embodiment and method, the non-wetted membrane is useful for controlling delivery of the drug until the catheter can be properly positioned within the tissue to be treated.

In the preferred embodiment, the apparatus includes a flexible member adapted for insertion into the body passageway and a drug delivery means connected with the flexible member for delivering the drug to or through a local area of the passageway wall. The drug delivery means includes a porous membrane for engagement with a local area of the passageway wall and a drug chamber for receiving a selected drug. The chamber is defined in part by the porous membrane which is constructed of a material that permits selective transport of a drug therethrough, i.e. constructed of a non-wetted membrane which is selectively permeable. By selectively permeable, it is meant that until the membrane is wetted it is essentially impermeable to the drug solution. After wetting, however, the membrane is permeable to the drug solution, thereby allowing drugs delivered through the catheter body to be released to the internal body tissue.

Preferably, in one embodiment the drug delivery means includes a modified catheter balloon or bag made of a non-wetted membrane. The modified catheter balloon contacts the inner surface of the passageway wall and defines the localized passageway area to or through which the drug is to be administered. After contact and/or dilatation, the membrane is wetted using wetting means, thereby causing the membrane to become permeable.

The method of the present invention involves positioning a drug delivery apparatus in a body passageway such that the delivery member or balloon traverses the desired localized area of administration. The balloon is then inflated or-otherwise expanded to define a local drug administration zone in the passageway. This involves introducing a non-wetting liquid into or through the localized zone or passageway. The method for delivering a drug to an internal body tissue involves removing the nonwetting liquid and supplying a wetting liquid; pressurizing the fluid to a point at which it wets the porous membrane; or providing another means such as electric current/voltage or ultrasonic energy to wet the porous membrane. Once the membrane is wetted transporting the selected drug across the now permeable wetted porous membrane and into the internal body tissue target area can proceed using pressure and/or phoresis assisted drug delivery.

A specific application of the apparatus and method of the present invention involves the treatment of a dilated vessel to prevent restenosis following PTCA. In the preferred embodiment and procedure, this involves administering a drug solution or fixative to the passageway walls in the localized area.

A further specific application of the apparatus and method of the present invention is in the treatment of cancerous tumors or other internal body tissue adjacent to a body passageway, such as the prostrate.

Accordingly, it is an object of the present invention to provide a drug delivery apparatus and method for simultaneously or sequentially dilating a passageway and delivering a drug or combination of drugs to a local area of the passageway using a single device.

It is also an object of the present invention to provide a drug delivery apparatus and method for delivering a drug or combination of drugs to a local area of internal target tissue in which delivery can be precisely controlled through the use of a non-wetted porous membrane.

DESCRIPTION OF THE DRAWINGS

FIG. 7 is a fragmentary view, partially in section, of a still further alternate design of a drug delivery apparatus in accordance with the present invention in the form of a catheter with a drug delivery component to transport a drug to an internal body tissue.

FIG. 8 is a fragmentary view, partially in section, of a still further alternate design of the drug delivery apparatus shown in FIG. 7 for drug transport to an internal body tissue in which a selectively permeable membrane forms a portion of the outer wall of the drug delivery component.

FIG. 9a shows an isotropic (asymmetric) structure. FIG. 9b shows a symmetric structure.

DESCRIPTION OF THE PREFERRED AND ALTERNATE EMBODIMENTS AND METHODS

Figure 1:
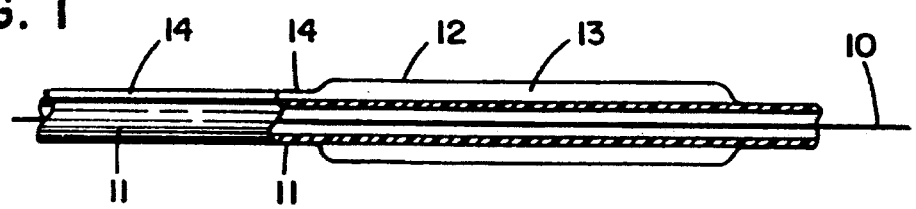
FIG. 1 is a fragmentary view, partially in section, of a first embodiment of the drug delivery apparatus of the present invention in the form of a catheter with a modified dilatation balloon in its deflated state.

FIGS. 1–6 illustrate the preferred and various alternate designs of the drug delivery apparatus in accordance with the present invention. In general, this apparatus provides a means and a system for dilating a passageway and delivering a drug or combination of drugs to or through a localized area of a passageway in order to treat the localized area of the passageway or to treat a localized area of tissue located adjacent to the passageway, with minimal, if any, undesirable effect on other body tissue.

As used in the present application, the term "drug" is intended to broadly include any medicament or other substance which is desired to be delivered to body tissue for therapeutic, diagnostic or any other purpose. The term "catheter" is intended to broadly include any medical device designed for insertion into a body passageway to permit injection or withdrawal of fluids, dilate a passage, keep a passage open, or for any other purpose. It is contemplated that the drug delivery apparatus of the present invention has applicability for use with any body passageways including, among others, blood vessels, urinary tract, intestinal tract, kidney ducts, wind pipe and the like.

FIGS. 7 and 8 illustrate further alternate designs of the drug delivery apparatus in accordance with the present invention. The embodiments shown in these figures are specifically designed to provide means and a system for delivering a drug or combination of drugs to a localized area of an internal body tissue. For this purpose the apparatus includes a flexible catheter connected to a drug delivery component having a fluid delivery lumen and a drug delivery chamber defined by a non-wetted porous membrane which, when wetted, allows a drug to pass from the drug delivery chamber to an internal body tissue target area.

In particular, catheters are commonly used in percutaneous transluminal coronary angioplasty (PTCA) procedures to dilate stenosed blood vessels or arteries. These include so-called over-the-wire catheters of the type illustrated generally in U.S. Pat. No. 4,323,071; fixed wire catheters of the type illustrated in U.S. Pat. No. 4,582,181; and rapid exchange catheters as illustrated in U.S. Pat. No. 4,762,129. The disclosure of each of the above patents is incorporated herein by reference. Any of the above catheters may be modified according to the present invention.

Furthermore, it will be understood that perfusion catheters may also be modified to provide localized internal drug delivery according to the present invention. One example of a perfusion catheter is disclosed in U.S. Pat. No. 4,892,519, which is hereby incorporated by reference.

In order to illustrate the method aspect of treating a localized area of a passageway, the specific application of the present invention to the reduction of restenosis will be described.

Percutaneous transluminal coronary angioplasty (PTCA) has been demonstrated to be a highly successful procedure for the treatment of atherosclerosis and other diseases and conditions tending to narrow arterial passageways. In normal PTCA procedure, a dilatation catheter is advanced along an artery to the desired position in the arterial system. The catheter includes an inflatable balloon formed of a non-porous membrane at its distal end and means for inflating the balloon. When the balloon is positioned so that it traverses or crosses a stenotic lesion, the balloon is inflated to compress the atherosclerosis and expand the artery in a direction generally perpendicular to its wall, thereby dilating the lumen of the artery. Following this procedure, the balloon is deflated and the catheter withdrawn.

Despite the generally excellent success of PTCA, relatively high restenosis (the tendency of the dilated artery to close) rates continue to be a major problem. Restenosis can include abrupt reclosure resulting from thrombotic occlusion, vasospasms, or the like as well as the more common occurrence of gradual restenosis.

In accordance with the method of the present invention, a drug referred to as a fixation solution or a fixative is delivered locally to the dilated portion of the vessel to render the vessel wall biologically inert to prevent or reduce reactions that lead to reclosure. Because of the nature of the fixative and its ability to inactivate living cells and render the tissue in which it comes into contact biologically inert, it is essential that such fixative be exposed only to that portion of the arterial wall which has been dilated.

The particular fixative or fixation solution as preferably contemplated by the present invention must be able to rapidly penetrate the plaque and vascular tissue of the vessel in the area of the stenotic lesion. It should quickly kill or otherwise preserve the tissue, while hardening the vascular structure. Such fixation maintains the vessel in an "opened" or dilated condition and prevents or substantially reduces reclosure due to vasospasm or other abrupt reclosure mechanisms. Such fixation also retards or stops the biological processes which lead to gradual restenosis. The preferred fixative should also have rapid, specific action in high concentrations, while generally nontoxic actions in lower concentrations.

The fixative or drug solution may include one or more of the following: antithrombotic, antiproliferative and antinflammatory agents; growth factor, smooth muscle cell migration and matrix degradation inhibitors; reendothelialization agent; or any other drug or agent that would eliminate, reduce or otherwise impede the restenosis of a vessel. Examples of antithrombotics include thrombin inhibitors such as hirudin, PPACK, hirulog, heparin, argatroban and platelet inhibitors such as 7E3 or other inhibitors of the platelet receptor GPIIb/IIIa. Examples of antiproliferative agents are antisense oligonucleotides, heparin and suramin.

A preferred method and apparatus for delivering the fixative locally to the dilated vessel is via a modified catheter balloon constructed according to the present invention. The balloon of the catheter that delivers the drug is the same balloon used to dilate the vessel, thus combining both functions in one balloon to minimize the time and expense associated with using a catheter with two balloons or two separate catheters. The present invention also eliminates the inherent problems of repositioning a second balloon in the same location as the first or, even more complicated, positioning a second catheter after the dilatation catheter has been withdrawn.

FIG. 1 illustrates the distal end of a catheter with the modified catheter balloon in its deflated state. The catheter includes a guide wire 10, an elongated, flexible catheter body 11, a drug delivery means in the form of a balloon 12 positioned on the catheter body 11 near its distal end and a balloon lumen or passageway 14 extending along the catheter body 11 to the proximal end of the body 11 for inflation and deflation of the balloon 12.

In the preferred embodiment, the material from which the balloon 12 is constructed is a non-wetted porous membrane which is effectively non-permeable in its non-wetted state. Once wetted, the membrane is permeable making it possible to transport a fixative or other drug across the membrane as a result of an appropriate driving force.

The structure of the guide wire 10, the catheter body 11 and the balloon lumen 14 is similar to conventional catheter design which is known in the art and an example of which is shown in U.S. Pat. No. 4,323,071. The balloon 12 of FIG. 1, however, is distinguishable from conventional catheter balloons in that the balloon 12 is constructed from a material described above briefly and which will be described in greater detail below.

As described above, the materials used to form known dilatation balloons are typically non-porous and impermeable to prevent leakage of the inflation fluid into the vasculature as well as to prevent pressure decay during the dilatation procedure. In devices according to the present invention, however, the membrane forming the balloon 12 of catheter 11 is preferably a non-wetted porous membrane which, although porous, is impermeable until the membrane becomes wetted. It is control over the wetting process which allows selective permeability in the membrane.

The wetting process can be controlled as the pressure at which pores in a porous material will wet is governed by the following equation:

$$P = (-4)(\gamma)(\cos \theta)/d$$

where:

P=applied pressure required to wet the pores

γ=surface tension of the liquid

θ=contact angle of the liquid on the membrane d=pore diameter

The above equation defines the pressure that is required for a fluid (having, for example, a contact angle greater than 90°) to wet the pores of the chosen membrane where the pore diameter, surface tension of the fluid, and the contact angle of the fluid on the surface of the membrane are known.

One porous membrane which is suitable for use with the present invention is a polyethylene film having a nominal pore size of 0.02 microns. At ambient pressures, water will not wet the pores of this film and will, instead, form a contact angle with the pores of about 95°. The surface tension of water is typically approximately 73 dynes/cm and, as such, the pressure required to wet the pores of this particular polyethylene film with water is approximately 185 psi (12.76 bar).

As a result, if the balloon 12 of the catheter 11 is made of the above described polyethylene film, the device could be used as a dilatation balloon and inflated with pressures up to 185 psi (12.76 bar) (assuming the inflating fluid is water or another fluid having a similar surface tension and forming a similar contact angle). Up to pressures of 185 psi (12.76 bar), the membrane would not exhibit permeability.

After the dilatation procedure was completed, the balloon material 12 could be made permeable by displacing the fluid within the balloon with a substitute solution having a lower surface tension to wet the pores of the film. One example of wetting fluid could be a 48% (by volume) ethanol solution in water which has a surface tension of approximately 28.9 dynes per centimeter at 40° C. The above fluid would wet the pores of the balloon 12 spontaneously.

Once the pores of the membrane 12 have been wetted, the wetting solution could be exchanged for a drug solution diagnostic fluid or other fluid. The membrane 12 would remain wetted and would be permeable to any succeeding fluid or solution. It will be understood that the above relationship applies to any porous film and non-wetting fluid and, as a result, a multitude of combinations are possible and will not be described further herein.

Other examples of means for wetting porous films which are non-wetted include adding low levels of surfactants to lower the surface tension of the fluid in contact with the film. Surfactants mixed in fluids to wet the membrane should be bio-compatible to avoid adverse reactions. One possible bio-compatible surfactant is sodium lauryl sulfate.

Figure 2:
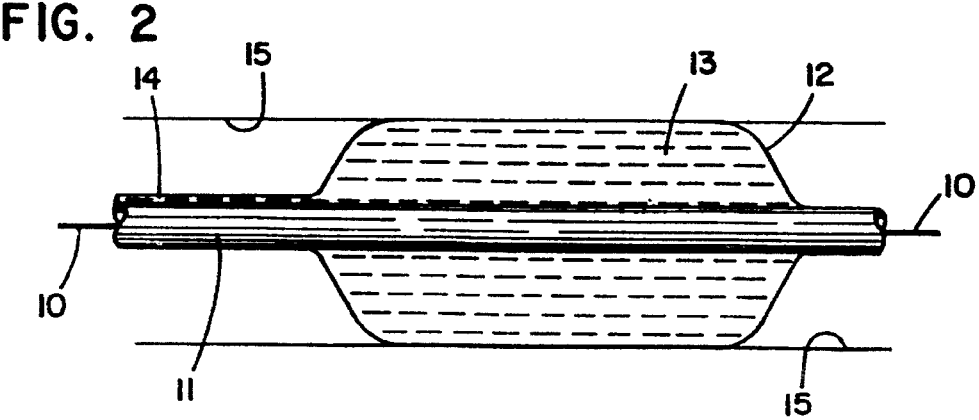
FIG. 2 is a fragmentary view, partially in section, of the drug delivery apparatus of FIG. 1 positioned in a blood vessel with the dilatation balloon in its inflated state.

FIG. 2 illustrates the drug delivery apparatus of FIG. 1 with the balloon 12 in its inflated state within an arterial vessel in which the vessel walls are indicated by the reference numeral 15. During PTCA procedures, the guide wire 10 is first inserted into the selected artery to a point past the stenotic lesion. The dilatation catheter including the catheter body 11 and balloon 12 is then advanced along the guide wire 10 to the desired position in the arterial system in which the balloon portion 12 traverses or crosses the stenotic lesion. The balloon 12 is then inflated by introducing an inflation fluid through the balloon lumen 14 into the interior chamber 13 of the balloon 12. During inflation, the outer surfaces of the balloon 12 press outwardly against the inner surfaces of the vessel wall 15 to expand or dilate the vessel in the area of the stenotic lesion. The pressure within the balloon 12 is maintained below the pressure required to wet the pores of the membrane forming balloon 12. Because the inflation fluid does not wet the pores of the balloon 12, none of the inflation fluid 13 leaks from the balloon 12.

After dilatation has been completed, the inflation fluid 13 is withdrawn and replaced with a wetting fluid having a lower surface tension to wet the pores of the balloon material 12. Alternatively, it will be understood that the pressure of the inflation fluid 13 could be raised to exceed the level at which the pores of the balloon 12 are wetted. In that way, the inflation fluid 13 does not need to be exchanged with a fluid having a lower surface tension for wetting.

In either instance, and because at least a portion of the balloon 12 being constructed of a membrane wetted according to the above procedures, the pressure of the drug or fixative within the balloon 12 causes the drug or fixative to be transported across the walls of the balloon 12 into direct contact with the vessel wall 15.

In the preferred embodiments, it is contemplated that the materials from which the porous membranes are constructed will be either normally hydrophobic materials or hydrophilic materials treated to exhibit hydrophobic properties at the surface of the membrane. Such treatments may include silicone or fluoropolymer coatings.

Furthermore, although the vast majority of solutions used with catheters according to the present invention will be water-based, making hydrophobic properties useful for controlling permeability through wetting, other solutions not based on water may be used in which case the membranes may exhibit non-wetting properties when exposed to those solutions (until the appropriate pressure is supplied). It will be understood that an unlimited number of combinations of fluids, membranes and pressures can be used to provide the desired wetting characteristics.

It is contemplated that the materials used for the membranes may include, without limitation, cellulose, cellulose acetate, polyvinyl chloride, polysulfone, polyacrylonitrile, silicon, polyurethanes, natural and synthetic elastomers. Examples of suitable microporous membrane materials are polyester, polyolefin, a fluoropolymer, or the like having pore sizes smaller than 3 microns, preferably from about 10 Å to about 1 micron, and even more preferably from about 50 Å to about 0.1 microns. Membranes with pore sizes in the most preferred range will be provided with a pore density in the range from about $10^4$ to about $10^{11}$ pores/cm$^2$, or more.

Furthermore, although non-elastomeric materials are preferred to provided controlled expansion and stable pore sizes, elastomeric materials may be used where their properties are desired.

It is contemplated that the particular material from which the balloon 12 is constructed will depend to some extent on the specific composition of the fixative or other drug and any carrier fluid to be delivered, as well as the transport or driving pressures which are developed within the balloon chamber 13. In the structure of FIGS. 1 and 2, the preferred material from which the balloon 12 is constructed is a hydrophobic thermoplastic. The pressure generated within the balloon chamber 13 to result in transport of the drug or fixative solution across the balloon walls varies depending on the means of wetting the membrane 12, which, as described above, can be pressure alone, or pressure in combination with a lower surface tension liquid.

In embodiments of the present invention designed for both dilatation and drug or fixative delivery, it is desired to use combinations of porous membranes with pore sizes and inflation fluids, drug solutions and/or fixative solutions which provide the ability to precisely control the pressure at which the membrane wets and, thus, becomes permeable. In some applications, it may be desirable to wet the membrane at pressures as low as about 10 psi (0.7 bar) where, for example, the user desires only to inflate the balloon prior to wetting the membrane. In other applications, it may be desirable to wet the membrane only at extremely high pressures, such as 185 psi or above.

For most vascular dilatation applications in which wetting occurs through increasing pressure, it is preferred that the pore size and fluids be chosen to provide wetting at pressures of up to approximately 90 psi (6.2 bar). In those applications in which wetting will be accomplished through a wetting agent or means other than increasing pressure alone, the pore size and fluids will generally be chosen to allow pressure to increase to about 60–150 psi (4.1–10.4 bar) or above without wetting the membrane. It will be understood that an unlimited number of combinations of fluids and membranes can be chosen to provide wetting at any desired pressure or pressure range.

Figure 3:
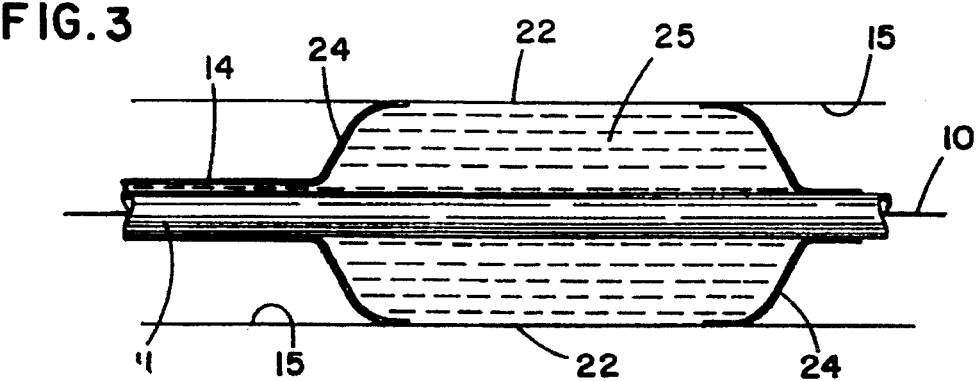
FIG. 3 is a fragmentary view, partially in section, of a further embodiment of the drug delivery apparatus of the present invention positioned in a blood vessel.
Figure 4:
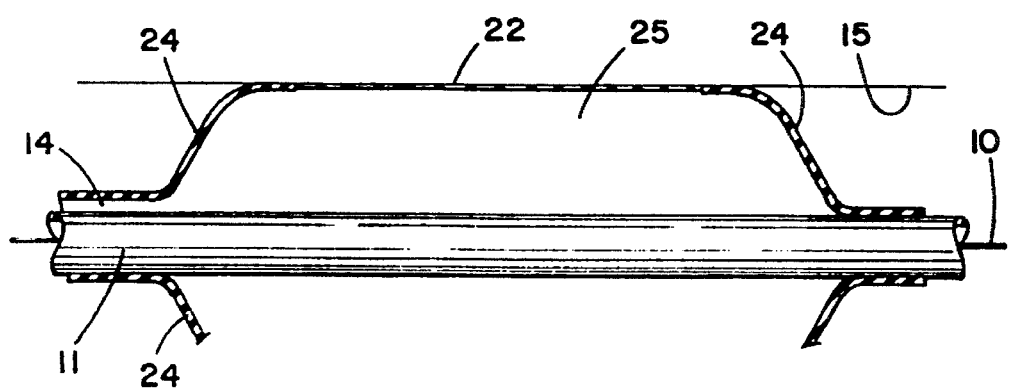
FIG. 4 is an enlarged fragmentary view, partially in section, of the embodiment of FIG. 3.

A further modified balloon structure is illustrated in FIGS. 3 and 4. The embodiment of FIGS. 3 and 4 is similar to the embodiment of FIGS. 1 and 2 except that the balloon structure in FIGS. 3 and 4 is constructed of two different materials. It will be appreciated that as an alternative, the balloon structure in FIGS. 3 and 4 can be constructed of one type of material that is modified in selected areas to include one or more impermeable portions. Possible modifications include, but are not limited to increased thickness, smaller pores which will be more difficult to wet, or no pores at all.

In FIGS. 3 and 4, the balloon end portions 24 are a totally impermeable material, while an intermediate portion 22 of the balloon positioned between the end portions 24 is a non-wetted porous material. The fixative or other drug is permitted to pass from the interior chamber 25 of the balloon only through the porous material 22 (after it has been wetted). The material from which the portion 22 is constructed is similar to the material from which the balloon 12 of FIGS. 1 and 2 and the outer balloon 18 of FIG. 3 is constructed. With the end portions 24 constructed of an impermeable material, inadvertent passage of the fixation solution or other drug through such end portions and along a longitudinal axis of the catheter is prevented.

Other variations in placement of the non-wetted porous material and impermeable material, such as radially restricting the non-wetted porous material to define a radial area of the passageway to which drug is delivered, will be understood to fall within the scope of the present invention. The purpose of any of these structures incorporating both impermeable and non-wetted porous materials is to enable more specific and precise delivery of the fixation solution or other drug desired to be administered.

If radially restricted delivery is desired, it will also be understood that additional sections of non-porous materials can be attached over a non-wetted porous membrane as is further discussed in U.S. patent application Ser. No. 07/956, 789, filed Oct. 5, 1992 and titled DRUG DELIVERY APPARATUS AND METHOD, which is hereby incorporated by reference.

In the structure of FIGS. 3 and 4, the impermeable material may be polyethylene, or polyester or an area of permeable material that is functionally impermeable because of increased thickness or other modification that results in a non-permeable region or regions.

As a further alternative, the catheters of FIGS. 1–5 may be coated on their outer surfaces, or at least that portion of the outer surface which is to contact the vessel wall, with hydrogel to improve contact with the vessel wall. The hydrogel so described may also contain the fixative or drug to be delivered where solution passing from the catheter through the hydrogel will dissolve the fixative or drug and transport the fixative or drug to the vessel wall.

In the embodiments of FIGS. 1–5, pressure is the force which is utilized to transport the fixative or other drug from the interior balloon chamber across the balloon wall to the vessel wall. However, it is contemplated that other transport forces could also be used either with or in lieu of pressure to enhance or otherwise control the speed of drug transport. For example, one method could utilize DMSO as a carrier to transport a fixative or drug through the vessel wall. Other fluid diffusion enhancement compositions include propylene glycol and ionic or non-ionic surfactants.

Another method could utilize iontophoresis technology. Such technology is known in the art and is commonly used in transdermal drug delivery. In general, iontophoresis technology uses an electrical potential or current across a semipermeable barrier to drive ionic fixatives or drugs or drag nonionic fixatives or drugs in an ionic solution. Iontophoresis can be useful in certain applications of the present invention because it facilitates both transport of the fixative or drug across the selectively permeable membrane after wetting and enhances tissue penetration.

Relating to the present invention, iontophoresis is also useful as an alternate means of wetting the non-wetted membrane. By passing an electric current through the membrane, the surface tension of the fluid is overcome, thereby wetting the membrane and allowing transport of the drug or fixative across the membrane.

In the application of iontophoresis, two electrodes, one on each side of the barrier, are utilized to develop the required potential or current flow. In particular, one electrode may be located inside of the catheter in opposed relation to the drug delivery wall of the catheter while the other electrode may be located at a remote site on a patient's skin. In addition to direct current, other wave-forms may be utilized (e.g., a series of rectangular waves producing a frequency of 100 Hz or greater).

Figure 5:
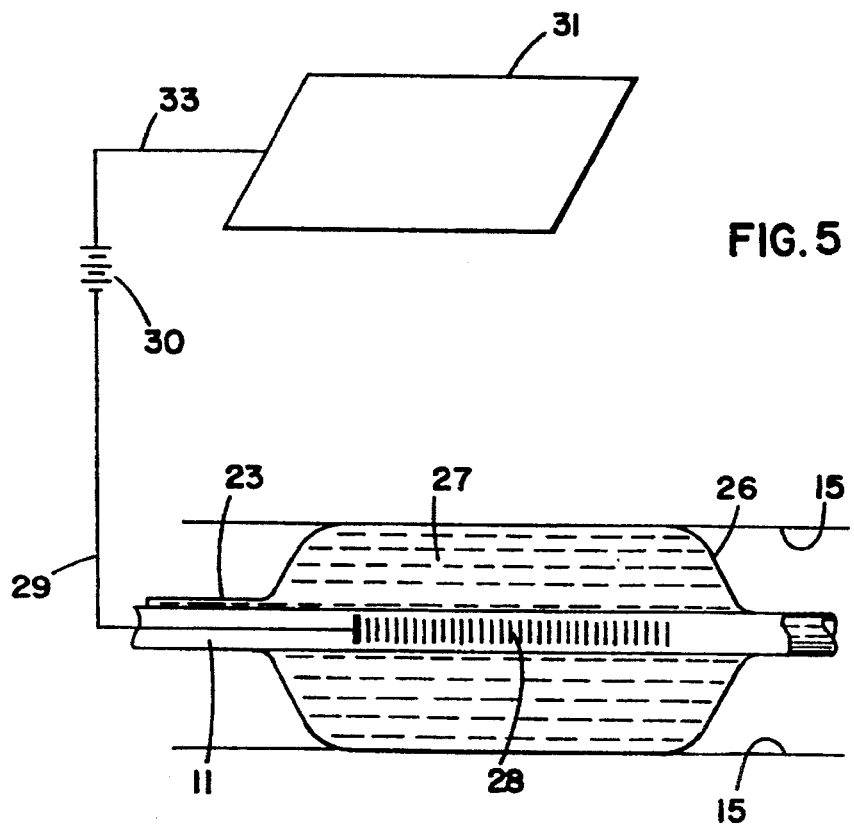
FIG. 5 is a fragmentary view, partially in section, of the drug delivery apparatus of the present invention positioned in a blood vessel and embodying iontophoresis means to transport the drug across the balloon surface.

The embodiment of FIG. 5 illustrates a structure utilizing iontophoresis to wet the membrane 26 and also assist in driving the fixative or other drug across the balloon wall 26 and into contact with the vessel walls 15. In FIG. 5, one electrode 28, the catheter electrode, is located on or within the catheter body 11 while the other electrode 31, the body surface electrode, is located on the body surface or within the body of the patient.

In order for iontophoresis techniques to be utilized, the fixative or other drug within the balloon chamber 27 requires specific characteristics. Ideally, such fixative or other drug should have an ionic nature or have other ionic molecules bound to the fixative or the active components of the drug to promote the iontophoretic or iontohydrokinetic movement or transport across the balloon wall 26. An electrical current for the iontophoretic process of FIG. 5 is produced between the electrodes 28 and 31 by an external power source 30 through the electrical leads 29 and 33, respectively.

During operation of the device of FIG. 5, the balloon 26 is first positioned across the stenotic lesion in the manner described above. The balloon interior 27 is then inflated with the fixative through the lumen 23 to a point below which the balloon wall 26 is not wetted. This is followed by activating the power supply 30, thereby creating a current between the electrode 28 and the electrode 31 which passes through the balloon wall 26. This current cause the fluid containing the fixative to wet the pores of the balloon wall 26 and, after wetting, drives or drags the fixative or other drug within the chamber 27 across the wall and into contact with the surrounding vessel wall 15 and vascular tissue. The structure of FIG. 5 utilizes both pressure and iontophoresis as the driving force, although, it is contemplated that iontophoresis could be utilized alone.

It will also be understood that the polarity of the iontophoretic electrodes may be reversed in order to recapture excess fixative or drug delivered to or through the vessel wall.

The use of iontophoresis to drive a drug across a membrane is further discussed in U.S. patent application Ser. Nos. 07/705,731 (filed 24 May 1991); 07/937,464 (filed 28 Aug. 1992); 07/957,209 (filed 6 Oct. 1992); and 08/110,109 (filed 20 Aug. 1993); all of which are hereby incorporated by reference for their disclosures relating to internal drug delivery catheters and methods regarding iontophoretic delivery.

Figure 6:
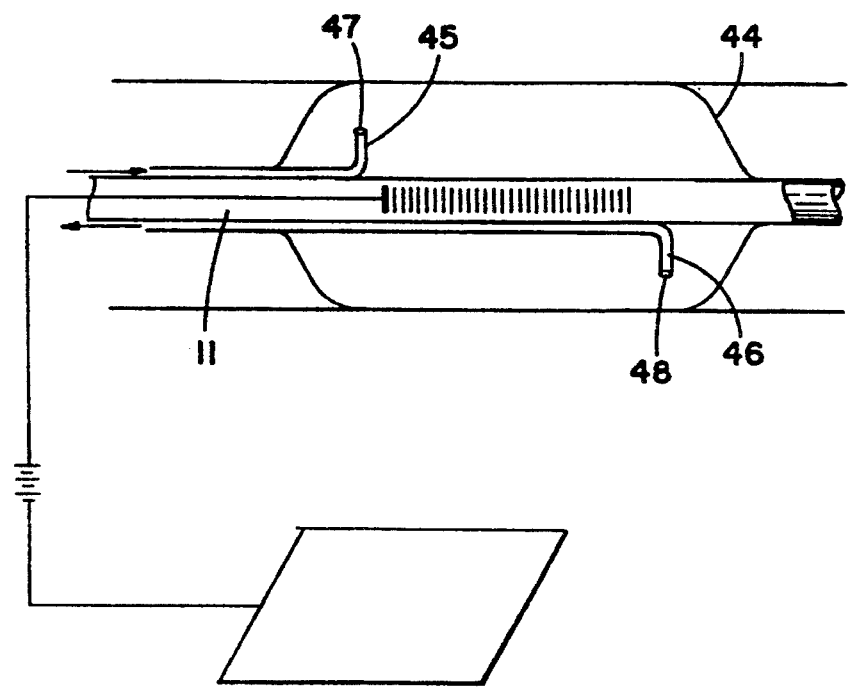
FIG. 6 is a fragmentary view, partially in section, of the drug delivery apparatus of the present invention positioned in a blood vessel, embodying iontophoresis to transport a drug across the balloon surface where the solution containing the drug is circulated through the balloon.

A still further embodiment of a drug delivery apparatus in accordance with the present invention is illustrated in FIG. 6. This embodiment would be useful for supplying and removing inflation fluids, wetting fluids and fixatives or other drugs and is useful for delivery of antitumor drugs.

FIG. 6 illustrates a modified catheter balloon design having a balloon 44 positioned on catheter body 11 near its distal end. One delivery lumen or passageway 45 extends along the catheter body 11 to the proximal end of the body 11 and a recovery lumen or passageway 46 also extends along the catheter body 11 to the proximal end, said delivery lumen 45 and recovery lumen 46 useful for circulating solution containing a fixative or drug to and from the catheter balloon. The outlets 47 and 48 may be positioned in the balloon to achieve optimal circulation within the balloon. This embodiment may be most useful in delivering antitumor drugs which are difficult to dissolve where the delivery solution accordingly is very low in concentration of the antitumor drug and easily depleted of such drug. Circulation in this case would be important for continuous delivery over long time periods. This embodiment may be combined with reversing the polarity of the electrodes of iontophoresis in order to remove excess drug after treatment.

In addition to the embodiment of FIG. 6, the embodiments of FIGS. 1–5, illustrated principally for delivery of a fixative to a vessel wall, can also be useful in delivering any drug to or through a vessel wall. In particular, each of the above embodiments of FIGS. 1–6 may be used for such drug delivery and each embodiment would be useful for delivering an antitumor, antihyperplastic or other agent through a vessel wall to a nearby or adjacent tumor or other internal body tissue. For example, a drug may be delivered substantially transversely to the longitudinal axis of a body passageway in order to treat a localized region of tissue located adjacent to the passageway. This is illustrated by using iontophoresis to drive, or DMSO to carry, through the passageway wall and into the surrounding or adjacent tissue. Any of the foregoing alternative embodiments of the apparatus as seen in FIGS. 1–6 may also be used for such drug delivery.

In particular, tumors may be treated by delivering certain drugs through blood vessels or the intestinal tract or whatever to adjacent tumor sites. For the purposes of primary or adjuvant treatment or other circumstances where drug delivery to a specific local or regional internal body tissue site such as a solid tumor, abscess, regional lymph nodes or the like is desired, further embodiments of the present invention as shown in FIGS. 7 and 8 are preferred. The tissue delivery system shown in FIGS. 7 and 8 includes a drug delivery apparatus 60 that is positioned into a specific tissue, such as a tumor.

As seen in FIG. 7, a preferred drug delivery apparatus 60 for treating an internal body tissue includes a flexible catheter body 11' and drug delivery component 69 having a drug delivery passageway 64 including an outer wall 66, and a non-wetted porous membrane portion 67 proximate the distal end 61. The impermeable nature of the non-wetted porous membrane 67 prevents escape of the drug from passageway 64 and drug delivery component 69 until the desired time of delivery. It is to be understood that the membrane 67 also controls the rate of release of the drug.

The membrane 67 is wetted according to the methods described above for wetting porous membranes. Once wetted, pressure and/or iontophoresis is used to drive the drug across membrane 67. In a preferred embodiment for iontophoresis, membrane 67 is constructed from a porous material which is either hydrophobic or hydrophilic with surface treated to exhibit hydrophobic characteristics. Drug delivery passageway 64 of drug delivery component 69 extends from proximal end 63 to distal end 61 of apparatus 60. As seen in FIGS. 7 and 8, preferably, drug delivery component 69 is coaxially aligned about catheter body 11' although radially restricted constructions are also contemplated. It is to be appreciated that drug delivery component 69 can be connected with catheter body 11' by a variety of adjacent configurations by one of skill in the art.

The embodiment seen in FIG. 7 illustrates membrane 67 affixed to a portion of outer wall 66 having at least one opening 68 to facilitate fluid transfer through passageway 64 to membrane 67. Alternatively, as seen in FIG. 8, the non-wetted porous membrane 67 can form an integral portion of outer wall 66. As seen in both FIGS. 7 and 8, to position apparatus 60 over the shaft of an introducer such as a probe, needle or trocar (not shown) introducer lumen 65 through the center of catheter body 11' is provided. It is to be understood that apparatus 60 can range in size from very large (trocar) to very small (tenths of mm), depending on the type and location of internal body tissue to be treated.

The embodiments of apparatus 60 in FIGS. 7 and 8 utilize iontophoresis to both assist in wetting of the membrane 67 as well as assist in driving the drug across selectively permeable membrane 67. To deliver a drug to a target area of an internal body tissue, iontophoresis is preferred because it facilitates both transport of a fixative or drug across the non-wetted porous membrane and enhances tissue penetration. If iontophoresis is used, then similarly to the structure seen in FIG. 5, one electrode 28', the catheter electrode, is located on or within catheter body 11', while the other electrode (31) is located on the body surface of the patient. The other electrode may in certain applications be positioned at other regions of the patient including appropriate internal areas.

As an alternative to the embodiments seen in FIGS. 7 and 8 using iontophoresis to deliver a drug to a target area, the tissue delivery system of the present invention can use pressure as the force to both wet the membrane and to transport a drug to a target area of internal body tissue. For this purpose, regulation means known to those skilled in the art (e.g., compressor, regulator or syringe pump) can be used to apply sufficient pressure to both wet the membrane and deliver the drug to the target area. Those of skill in the art will recognize that the pressure applied to wet the membrane 67 and drive the drug across the membrane 67 to the target area should not cause further traumatization of the internal body tissue to be treated.

As described earlier with respect to the embodiments shown in FIGS. 1–5, other means of wetting and transport forces can be used either with or in lieu of pressure to enhance or otherwise control both wetting of the membrane 67 and the speed of drug transport to an internal body tissue according to the present invention. For example, one of skill in the art could utilize DMSO, propylene glycol or various surfactants as a carrier to transport the drug through selectively permeable membrane portion 67 to the target area of internal body tissue. In addition the surfactants could be used to wet the membrane 67 or other wetting fluids could be introduced to lower the pressures at which membrane 67 wets, relying on the equation discussed earlier.

For treatment of an internal body tissue according to the present invention, the introducer (not shown) is placed into the target area, which may be a tumor or the like, after identification of the position of the lesion mechanically, radiographically, thermally, ultrasonically, or through some other like methodology. The trocar/probe can be designed for steerability to facilitate positioning into the tumor. This can be accomplished by simply placing a bend in the trocar or by other mechanical design techniques known to those skilled in the art.

The active apparatus 60 is then passed through or over the introducing element directly over the inducer or through the void left in the intervening tissue by the withdrawal of the introducer. After apparatus 60 is in place, as confirmed by one of the foregoing methods, the active compound is delivered through passageway 64 into drug compartment 69 and across membrane 67 into the local or regional tissue. Using an embodiment of apparatus 60 of the type seen in FIGS. 7 or 8, the delivery is accomplished iontophoretically. The active compounds delivered to an internal body tissue using apparatus 60 include, but are not limited to, antitumor agents such as the vinca alkaloids, anthracycline antibiotics, platinum analogs, antimetabolites (e.g., methotrexate); antibiotics; sensitizers or other similar compounds.

The advantage of this method is that it allows delivery of the drug into the interstitial fluid and into the cells of the target area themselves even if the vasculature of the area is severely compromised and the cells do not preferentially take up the drug. These phenomena are a well-known attribute of solid tumors and constitute one of the most significant barriers to the treatment of such cancers.

In addition to delivery of antitumor agents to internal tissues, the usefulness of the present apparatus and method for the treatment of other diseases of internal tissue will be appreciated by those skilled in the art.

In the case of both the vascular delivery embodiment (FIGS. 1–6) and tissue delivery embodiment (FIGS. 7 and 8) described herein, phonophoresis (sometimes referred to as sonophoresis) can be used as an alternative means for wetting the porous membranes and/or transporting drugs or fixatives across them.

Phonophoresis is the use of ultrasonic or high frequency sound waves to transport drugs. As used in the present invention, phonophoresis can be used to wet the membrane and/or to transport drugs through the selectively permeable membrane and into the surrounding tissue. For certain therapeutic procedures, phonophoresis has several advantages over iontophoresis, including the ability to achieve greater tissue penetration and to more readily deliver an entire molecule, rather than an ionically charged form of the drug. All prior applications of phonophoresis have been limited to transdermal delivery of drugs. It has primarily been used to deliver anti-inflammatory agents and local anesthetics through the skin in treating epicondylitis, tendinitis, bursitis and osteoarthritis.

Phonophoresis is, however, also well-suited for driving fixatives or drugs across the catheter of this invention to localized body passageways or internal tissues because it can be used to facilitate wetting of porous membranes, transport of a fixative or drug across the porous membrane, and enhances tissue penetration.

In addition to drug delivery, ultrasound may be advantageously used with the catheter of the present invention based on the increased tissue temperature, tissue hyperemia and increased capillary permeability associated with ultrasound. These actions can enhance intra-tissue drug transport and cellular uptake as well as cause vasodilation/relaxation which may be beneficial in vascular drug applications using catheter embodiments of the type described herein.

Figure 10:
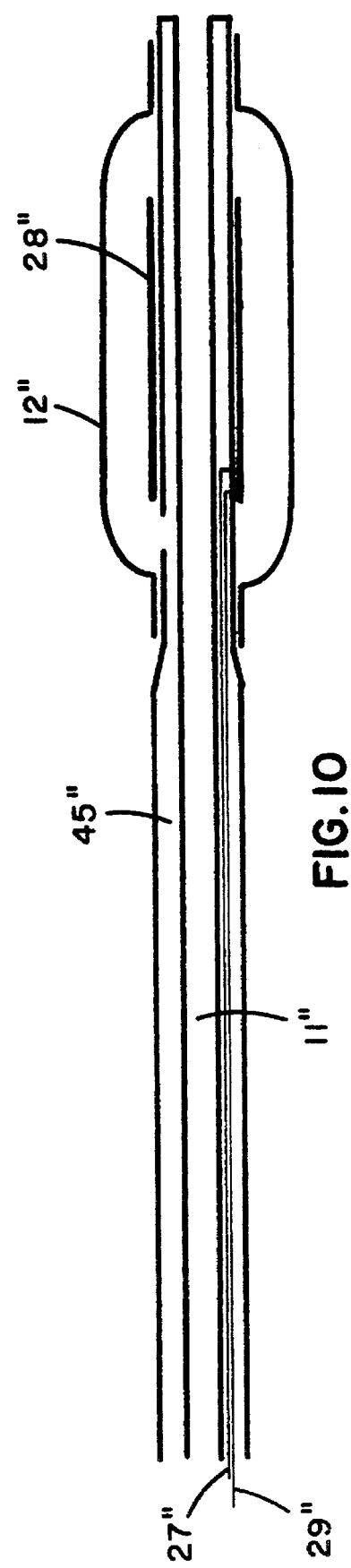
FIG. 10 is a fragmentary cross-sectional view of a drug delivery apparatus according to the present invention incorporating an ultrasonic transducer.

When phonophoresis is used with either the vascular delivery embodiment or tissue delivery embodiment of the catheter of the present invention, the cathode electrode 28 of FIG. 5 is replaced by an ultrasonic piezoelectric transducer (barium titanate, lead zirconate titanate, or the like), which is connected to the external power source 30 and placed within the catheter opposite the drug delivery wall. Reference is made to FIG. 10, which depicts an ultrasonic transducer 28" provided coaxial with the catheter body and connected to the proximal end of the catheter by leads 27" and 29". The ultrasonic transducer 28" is activated to enhance transport of drugs or fixatives into tissue surrounding the catheter.

The diffusion rate of drugs delivered by phonophoresis depends upon the intensity and frequency of the ultrasonic field. Prior transdermal applications of phonophoresis use intensities of 0.1 to 6 watts/cm and involve direct correlation between the amount of drug diffused and the intensity of the ultrasonic field. Internal applications (not requiring transdermal delivery) of phonophoresis with the catheter embodiments of the present invention are envisioned to require significantly less intensity to deliver an equal amount of drug. Various frequencies can be used. A frequency of about 1 MHz has been optimally used in transdermal phonophoresis. It is envisioned that approximately 1 MHz or more can be used for internal applications of the catheter embodiments described herein.

The use of phonophoresis-assisted internal drug delivery using catheters is further described in U.S. patent application Ser. Nos. 07/705,731 (filed 24 May 1991) and 07/937,464 (filed 28 Aug. 1992); both of which are hereby incorporated by reference for their disclosures relating to internal drug delivery catheters and methods regarding phonophoretic delivery.

According to the present invention, the above-described catheter embodiments are envisioned employing a porous membrane with non-wetted pores, making the membrane effectively non-permeable until the pores are wetted. The porous membrane, in conjunction with the active delivery mechanisms, aids in controlling drug transfer from the catheter by eliminating passive diffusion or flow under the pressure involved in filling the drug chamber or inflating the balloon to make contact and dilate with a vessel wall. Drug delivery into the tissue under active iontophoretic or phonophoretic delivery will not, however, be inhibited by the membrane.

One subset of porous membranes suitable for use with the present invention are microporous membranes. When compared to porous membranes, microporous membranes can provide more controlled delivery areas which, in turn, provide more uniform drug distribution into the surrounding tissue. If iontophoresis is used, the microporous membrane will also reduce the potential for areas of high current densities during iontophoresis (associated with porous balloons containing a relatively low number of relatively larger pores) and will also decrease the potential for tissue damage or breakdown of the membrane material due to high current density.

The numerous micropores will reduce the likelihood that a significant portion of the membrane could become blocked with blood components, secretions, lubricants, or other material. In addition, blood or other secretions will not cross the microporous membrane and enter the drug chamber during deflation of the balloon. The microporous material will also allow rapid balloon deflation without blood reflux into the catheter, which is an important feature in coronary arterial applications. The microporous material will also allow the use of a neutral or charged membrane surface to promote or control drug transfer and delivery. Furthermore, the pore sizes are typically small enough to prevent wetting with many fluids even at the substantial pressures which may be needed to perform the required dilatation.

Figure 9A:
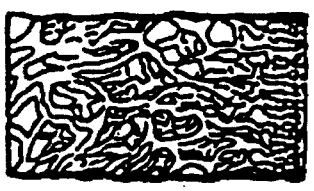
FIGS. 9a and 9b show partial cross-sections of two microporous membranes useful with catheters constructed according to the present invention.
Figure 9B:
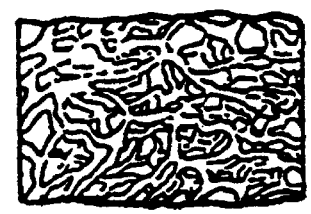

A schematic structure for the microporous membrane is illustrated in FIGS. 9a and 9b. Particularly, the microporous membrane can have either an isotropic (asymmetric) or symmetric structure. The pore size of the microporous membrane can vary from about 10 Å to 30,000 Å (i.e., 3 microns) or more.

Microporous membranes that satisfy the requirements of the present invention can be manufactured in any of several ways, most of which are readily understood by those skilled in the art of manufacturing microfiltration and ultrafiltration membranes. These techniques include, for example:

1. A phase inversion process in which an appropriate polymer solution is coagulated in a nonsolvent quench bath can be employed.
2. A thermal inversion process can be used whereby a polymer solution or mixture at elevated temperatures can be coagulated by a reduction in temperature, under controlled conditions, to form a microporous membrane.
3. A so-called track-etch process whereby a polymer film is bombarded by protons, electrons, radiation, etc. and then subsequently subjected to a controlled etching can be used as well.
4. A laser may be used to form holes or pores of the desired size in a polymeric material.

In both processes 1 and 2, conditions can result in either a symmetric or an asymmetric membrane being formed. Either type of membrane can be useful, although a preference may exist for one or the other in a given application. Any post-treatment of the membranes, such as irradiation, chemical grafting, coatings, etc. that would render the membrane more hydrophobic, fouling resistant, form a thin-film composite membrane or impart any other desirable properties would be a possible supplement to the above-mentioned formation processes. These processes are examples of methods that can be used to form a membrane of the desired properties. However, any additional methods that currently exist or that may become apparent that produce the desired membrane properties should also be included in the possible membrane formation mechanisms.

There are several forms or geometries into which these membranes can be made. A flat sheet membrane can be made into a balloon shape or cylinder by gluing, sonic welding, etc. Additionally, a hollow fiber membrane can be spun or a tubular membrane cast that can be used as is or processed into a balloon by blow molding or some other balloon-forming process. A third option is to cast the membrane directly into a balloon shape by spin-casting or some other process that allows the desired shape to be achieved. During this processing, a membrane support can be used if desired or required. Yet another option is to make the membrane directly from a reformed balloon.

One embodiment of the present invention incorporating a microporous membrane is shown in FIGS. 3 and 4. This embodiment includes a drug delivery component in the form of a balloon which contacts the body tissue for drug delivery. The balloon is preferably made of an inelastic material such as polyester, polyolefin, a fluoropolymer, or the like. Preferably, the balloon includes a hydrophobic microporous membrane portion 22 and an impermeable section 24 as best shown in FIGS. 3 and 4. The drug delivery component is formed proximate the distal end of the catheter and can include an active, non-pressure transport force such as iontophoresis (FIG. 5) or phonophoresis (FIG. 10).

The above detailed description has disclosed the use of wetting solutions with low surface tensions, pressure, surfactants, iontophoresis and phonophoresis as means for wetting the non-wetted porous membranes of devices constructed according to the present invention. It will be understood that other means of wetting, such as increasing the temperature of the fluid within the membrane can also be used as the means of wetting and that the disclosed means should not be considered restrictive of the actual means used to wet the non-wetted porous membranes.

Furthermore, although the descriptions of the preferred embodiments and methods have been quite specific, it is contemplated that various modifications could be made without deviating from the spirit of the present invention. Accordingly, it is intended that the scope of the present invention be dictated by the appended claims, rather than by the descriptions of the preferred embodiments and methods.

We claim:

1. A method of delivering a drug to internal body tissue, comprising the steps of:
   (a) providing a catheter having a non-wetted and controllably permeable porous membrane proximate said distal end of said catheter, said membrane having a predetermined pore size and defining a drug delivery chamber at said distal end of said catheter;
   (b) positioning said drug delivery chamber proximate said internal body tissue;
   (c) wetting said porous membrane with a fluid thereby making said membrane permeable, said fluid having a predetermined surface tension and a predetermined contact angle with the porous membrane; and
   (d) transporting said drug from said delivery chamber to said internal body tissue across said porous membrane.

2. The method of claim 1, wherein said step of positioning further comprises positioning said drug delivery chamber in an internal elongated passageway proximate said internal body tissue.

3. The method of claim 2, further comprising the step of dilating said passageway by expanding said porous membrane.

4. The method of claim 1, wherein said step of wetting further comprises providing a fluid to said drug delivery chamber through said fluid delivery lumen.

5. The method of claim 4, wherein providing said fluid further comprises providing a wetting agent in said fluid.

6. The method of claim 5, wherein providing said wetting agent further comprises providing a surfactant in said fluid.

7. The method of claim 4, wherein said step of wetting further comprises pressurizing said fluid.

8. The method of claim 4, wherein said step of wetting further comprises providing a voltage gradient from said fluid in said drug delivery chamber to said internal body tissue across said porous membrane.

9. The method of claim 1, wherein said step of transporting further comprises providing a voltage gradient from said drug delivery chamber to said internal body tissue across said porous membrane.

* * * * *